United States Patent [19]
Potter et al.

[11] Patent Number: 6,054,594
[45] Date of Patent: Apr. 25, 2000

[54] PROCESS FOR THE PRODUCTION OF ENANTIOMERICALLY ENRICHED N-ACYLAZETIDINE-2-CARBOXYLIC ACIDS

[75] Inventors: Gerard Andrew Potter; Michael C. J. Harris, both of Cambridge, United Kingdom

[73] Assignee: Astra AB, Sodertalje, Sweden

[21] Appl. No.: 09/202,503

[22] PCT Filed: Jul. 15, 1997

[86] PCT No.: PCT/GB97/01915

§ 371 Date: Dec. 16, 1998

§ 102(e) Date: Dec. 16, 1998

[87] PCT Pub. No.: WO98/02417

PCT Pub. Date: Jan. 22, 1998

[30] Foreign Application Priority Data

Jul. 15, 1996 [GB] United Kingdom .................. 9614804

[51] Int. Cl.⁷ .............................................. C07D 205/04
[52] U.S. Cl. ............................................................ 548/953
[58] Field of Search ............................................. 548/953

[56] References Cited

U.S. PATENT DOCUMENTS 4,230,719 10/1980 Kodama et al. ........................ 424/275
5,473,075 12/1995 Ohara et al. ............................ 546/173
5,866,568  2/1999 Bradbury et al. ..................... 514/227.8

OTHER PUBLICATIONS

Resolution of DL–Azetidine–2–carboxylic Acid, Richard M. Rodebaugh and Norman H. Crommell, Journal of Heterocyclic Chemistry, vol. 6, No. 6, pp. 993–994, Dec. 1969.

R.M. Rodebaugh: "Resolution of DL—Azetidine—2—carboxylic acid" Journal of Heterocyclic Chemistry, vol. 5, No. 6, 1969, Provo, US, pp. 993–994.

Chemical Abstracts, Vol. 82, No. 26, 30 Jun. 1997, Columbus, Ohio, US; abstract No. 171620, Boni R., et al: "Conformational properties of poly(L—azetidine—2—carboxylic acid) in solution as studied by carbon—13 and proton nuclear Magnetic resonance spectroscopy".

J.S. Davies et al.: "Conformational features of benzoyl N—alkylated amino—acids determined by nuclear magnetic resonance spectroscopy", Journal of The Chemical Society Perkin Transactions II, Vol. 11, 1978, pp. 1157–1163.

Mitsuru Furukawa et al.: "Asymmetric syntheses of beta—amino acid and aspartic acid by Reformatsky reaction", Chemical and Pharmaceutical Bulletin, Vol. 26, 1978, Tokyo, pp. 260–263.

Primary Examiner—Robert W. Ramsuer
Attorney, Agent, or Firm—Nixon & Vanderhye

[57] ABSTRACT

Process for obtaining an enantiomerically enriched N-acylazetine-2-carboxylic acid by selectine crystallization of a diastereoisomeric salt formed by relcting an enantiomer of the N-acylazetidine-2-carboxylic acid and an enantiomer of 1-phenylethylamine.

2 Claims, No Drawings

PROCESS FOR THE PRODUCTION OF ENANTIOMERICALLY ENRICHED N-ACYLAZETIDINE-2-CARBOXYLIC ACIDS

FIELD OF THE INVENTION

This invention relates to a novel process for the production of enantiomerically enriched N-acylazetidine-2-carboxylic acids.

BACKGROUND TO THE INVENTION

Azetidine-2-carboxylic acid is an unusual amino acid, the (S)-enantiomer of which is known to be useful in the synthesis of inter alia high molecular weight polypeptides and in particular as an analogue of the well known amino acid proline.

This amino acid is of limited availability from natural sources, and in nature is found only as the (S)-enantiomer. The development of an efficient and economic synthetic method for producing both the pure racemic compound and either of the individual (R) or (S) single enantiomers is therefore desirable.

Previously documented chiral syntheses of (S)-azetidine-2-carboxylic acid include a five step preparation via homoserine lactone, starting from N-tosyl protected L-methionine (see e.g. Japanese Patent Application No. 14457/74 and Bull. Chem. Soc. Jpn. (1973) 46, 699) and a five step preparation via L-4-amino-2-chlorobutyric acid, starting from L-2,4-diaminobutyric acid (see Biochem. J. (1956) 64, 323).

Previously documented preparations of enantiomerically-pure azetidine-2-carboxylic acid from the racemate involve long and relatively complicated multi-step methodology.

For example, a four step preparation involving the protection, resolution and subsequent deprotection of racemic azetidine-2-carboxylic acid is known from J. Heterocyclic Chem. (1969) 6, 993. In this method, N-carbobenzoxy-protected racemic azetidine-2-carboxylic acid is resolved, using L-tyrosine hydrazide as resolution agent, and then isolated before a final deprotection step. This process has the disadvantage that L-tyrosine hydrazide is expensive as well as only being available in one enantiomeric form. This prior art also reports the additional problem that attempts to use common resolving agents in the resolution of several N-acyl derivatives of racemic azetidine-2-carboxylic acid results in the production of non-crystallizable oils.

Surprisingly we have found that N-acyl derivatives of azetidine-2-carboxylic acids may be efficiently and economically resolved using the common and inexpensive resolving agent 1-phenylethylamine.

DESCRIPTION OF THE INVENTION

According to the invention there is provided a process for obtaining an enantiomerically enriched N-acylazetidine-2-carboxylic acid, which comprises the selective crystallisation of a diastereoisomeric salt formed between the required enantiomer of the N-acylazetidine-2-carboxylic acid and an enantiomer of I-phenylethylamine (hereinafter referred to as "the process according to the invention").

Enantiomerically enriched N-acylazetidine-2-carboxylic acids may be obtained routinely from distereolsomeric salt products of the process according to the invention using methods which are well known to those skilled in the art, such as treatment of such a salt with a strong acid.

By "enantiomerically enriched" we mean any mixture of the enantiomers of an N-acylazetidine-2-carboxylic acid in which one enantiomer is present in a greater proportion than the other, for example mixtures with an enantiomeric purity (enantiomeric excess; e.e.) of greater than 50%, preferably at least 70% and more preferably at least 90%.

Preferred N-acyl derivatives of azetidine-2-carboxylic acid include the N-benzoyl derivative.

The process according to the invention is effected by seeding a supersaturated solution of a salt between a racemic N-acylazetidine-2-carboxylic acid and one or other enantiomer of 1-phenylethylamine with crystals of the pure diastereoisomeric salt formed between that enantiomer of 1-phenylethylamine and the required enantiomer of the N-acylazetidine-2-carboxylic acid.

By "pure diastereoisomeric salt" we mean a salt formed between an enantiomer of 1-phenylethylamine and an enantiomer of an N-acylazetidine-2-carboxylic acid with a diastereoisomeric excess (d.e.) of greater than 90% and preferably greater than 96%.

The process according to the invention may be optimised non-inventively by the skilled person in order to enhance process efficiency, as well as increasing the yield, and enantiomeric purity, of the diastereoisomeric salt product. The process according to the invention may thus be carried out in a variety of solvents including aqueous and, particularly, organic solvents which do not interfere with the resolution process, or mixtures of such solvents. Preferred solvents include ethyl acetate. The process according to the invention may also be carried out over a temperature range of between −20° C. and the boiling point of the solvent system which is employed. The process according to the invention may further be carried out without, or with, stirring, the rate of which may be varied.

The process according to the invention may also be used for enantiomeric enrichment, i.e. enhancing the enantiomeric excess of a partially resolved N-acylazetidine-2-carboxylic acid, for example following a partial resolution process or an asymmetric synthesis.

The N-acyl group of the enantiomerically enriched acid may subsequently be removed in order to produce enantiomerically pure azetidine-2-carboxylic acid in accordance with techniques which are well known to those skilled in the art, for example by hydrolysis in the presence of alkali. Saponification may be carried out in this way in aqueous media, at between room temperature and 100° C., in the presence of an appropriate alkali (e.g. an alkali metal hydroxide, such as lithium, sodium and potassium hydroxide). We have found, advantageously, that saponification of the enantiomerically enriched N-acylazetidine-2-carboxylic acid (and, in particular, the N-benzoyl derivative) proceeds without racemization.

The process according to the invention may thus be used as part of a process to produce enantiomerically enriched azetidine-2-carboxylic acid.

According to a further aspect of the invention there is provided a process for the production of enantiomerically enriched azetidine-2-carboxylic acid, which process comprises a selective crystallisation as hereinbefore defined, followed by removal of the N-acyl group.

The process according to the invention may be used to produce either the (R)- or the (S)-azetidine-2-carboxylic acid. However, in view of the aforementioned utility of the (S)-enantiomer we prefer that the process according to the invention is used in the production of the latter.

The process according to the invention has the advantage that 1-phenylethylamine is readily available in either enantiomeric form. Moreover, either enantiomer of 1-phenylethylamine may be used in the selective crystallisation of (R)- or (S)-N-acylazetidine-2-carboxylic acid salts with equal facility. Furthermore, the process according to the invention is operationally simple and is suitable to large scale resolution.

EXAMPLE

Resolution of the Salt of (S)-N-Benzoylazetidine-2-carboxylic Acid and (−)-1-Phenylethylamine To a solution of racemic N-benzoylazetidine-2-carboxylic acid (500 mg, 2.4 mmol) in ethyl acetate (3 ml) was added (−)-1-phenylethylamine (295 mg, 2.4 mmol). To the resulting solution was then added seed crystals of the single diastereoisomer of the salt between (−)-1-phenylethylamine and (S)-N-benzoylazetidine-2-carboxylic acid (7 mg). Stirring was continued for 3 h and the resultant crystals collected by filtration to give the salt of (S)-N-benzoylazetidine-2-carboxylic acid and (−)-1-phenylethylamine with a d.e. of 91% (252 mg).

What is claimed is:

1. A diastereoisomeric salt formed between an enantiomer of an N-acylazetidine-2-carboxylic acid and an enantiomer of 1-phenylethylamine.

2. A salt as claimed in claim 1, characterised in that the acyl group is benzoyl.

* * * * *